(12) United States Patent
Chudzik et al.

(10) Patent No.: US 7,968,614 B2
(45) Date of Patent: Jun. 28, 2011

(54) MACROMER COMPOSITION INCLUDING LIGHT ACTIVATED INITIATOR

(75) Inventors: Stephen J. Chudzik, St. Paul, MN (US); Michael J. Burkstrand, Richfield, MN (US)

(73) Assignee: Surmodics, Inc., Eden Prairie, MN (US)

( * ) Notice: Subject to any disclaimer, the term of this patent is extended or adjusted under 35 U.S.C. 154(b) by 716 days.

(21) Appl. No.: 11/453,494

(22) Filed: Jun. 15, 2006

(65) Prior Publication Data

US 2006/0287410 A1 Dec. 21, 2006

Related U.S. Application Data

(60) Provisional application No. 60/690,706, filed on Jun. 15, 2005.

(51) Int. Cl.
C08F 2/46 (2006.01)
A61K 6/08 (2006.01)

(52) U.S. Cl. ........ 522/47; 523/118; 427/487; 433/228.1

(58) Field of Classification Search .......... 523/118; 522/47; 427/487; 433/228.1
See application file for complete search history.

(56) References Cited

U.S. PATENT DOCUMENTS

| | | | |
|---|---|---|---|
| 4,880,660 A | 11/1989 | Aasen et al. | |
| 5,410,016 A * | 4/1995 | Hubbell et al. | 528/354 |
| 5,595,487 A * | 1/1997 | Ario et al. | 433/226 |
| 5,749,968 A | 5/1998 | Melanson et al. | |
| 5,837,752 A | 11/1998 | Shastri et al. | |
| 5,844,016 A | 12/1998 | Sawhney et al. | |
| 5,866,630 A | 2/1999 | Mitra et al. | |
| 5,900,245 A | 5/1999 | Sawhney et al. | |
| 6,031,017 A | 2/2000 | Waki et al. | |
| 6,051,626 A | 4/2000 | Zeng et al. | |
| 6,224,893 B1 | 5/2001 | Langer et al. | |
| 6,313,189 B1 * | 11/2001 | Wenz et al. | 522/179 |
| 6,387,977 B1 | 5/2002 | Sawhney et al. | |
| 6,410,044 B1 | 6/2002 | Chudzik et al. | |
| 6,437,065 B1 | 8/2002 | Ritter et al. | |
| 6,531,147 B2 | 3/2003 | Sawhney et al. | |
| 6,596,403 B2 | 7/2003 | Mitra et al. | |
| 6,664,306 B2 | 12/2003 | Gaddam et al. | |
| 6,669,994 B2 | 12/2003 | Swan et al. | |
| 2002/0120033 A1 * | 8/2002 | Jia et al. | 523/115 |
| 2003/0087986 A1 * | 5/2003 | Mitra | 523/116 |
| 2003/0114552 A1 | 6/2003 | Schacht et al. | |
| 2004/0091462 A1 | 5/2004 | Lin et al. | |
| 2005/0112086 A1 | 5/2005 | Swan et al. | |
| 2005/0255142 A1 | 11/2005 | Chudzik et al. | |
| 2006/0160919 A1 * | 7/2006 | Brugger et al. | 523/116 |
| 2007/0009449 A1 * | 1/2007 | Kanca, III | 424/49 |

FOREIGN PATENT DOCUMENTS

| | | |
|---|---|---|
| JP | 2003/169844 | 6/2003 |
| WO | WO 93/16687 | 9/1993 |
| WO | WO 98/12243 | 3/1998 |
| WO | WO 02/100453 | 12/2002 |
| WO | WO 2004/031253 | 4/2004 |
| WO | WO 2004/075862 | 9/2004 |
| WO | WO 2005/054304 | 6/2005 |

OTHER PUBLICATIONS

International Search Report for International Application No. PCT/US2006/023458, mailed Jul. 2, 2007, 5 pgs.
Okino, et al., "In situ Hydrogelation of Photocurable Gelatin and Drug Release," Journal of Biomedical Materials Research, vol. 59, No. 2, 2002, pp. 233-245.
Cailong, et al., "Novel Visible-Light-Induced Photocurable Tissue Adhesive Composed of Multiply Styrene-Derivatized Gelatin and Poly(ethylene glycol) Diacrylate," Jounal of Biomedical Materials Research, Part B, Applied Biomaterials, vol. 66B, No. 1, 2003, pp. 439-446.
Matsuda, et al., "Preparation of Vinylated Polysaccharides and Photofabrication of Tubular Scaffolds as Potential Use in Tissue Engineering," Biomacromolecules, vol. 3, No. 5, 2002, pp. 942-950.
Pande, et al., "Camphorquinone-10-Sulfonic Acid and Derivatives: Convenient Reagents for Reversible Modification of Arginine Residues," National Academy of Sciences, vol. 77, No. 2, Feb. 1, 1980.
Kwang-Duk Ahn, et al., "New Aromatic tert-Amines for Application as Photoinitiator Components in Photocurable Dental Materials," Macromol. Chem. Phys., vol. 204, No. 13, 2003, pp. 1628-1635.
Gatej, et al., "Role of the pH on Hyaluronan Behavior in Aqueous Solution," Biomacromolecules, vol. 6., No. 1., 2005, pp. 61-67.
Engstrom, et al., "The Effect of Hyaluronan on Bone and Soft Tissue and Immune Response in Wound Healing," J. Periodontol, vol. 72, No. 9, Sep. 2001, pp. 1192-1200.
Nakayama, et al., "Newly Designed Hemostatic Technology Based on Photocurable Gelatin," Am Soc Artif Intern Org J, 1995; 41:374-378.
Leach, et al., "Photocrosslinked Hyaluronic Acid Hydrogels: Natural, Biodegradable Tissue Engineering Scaffolds," Biotechnology and Bioengineering, vol. 82, No. 5, 2003, pp. 578-589.

* cited by examiner

*Primary Examiner* — Tae H Yoon
(74) *Attorney, Agent, or Firm* — Kagan Binder, PLLC

(57) ABSTRACT

The invention provides compositions that include macromers and visible light-activated polymerization initiators, and methods for forming a matrix using these compositions in conjunction with a light source that emits light primarily in the visible light spectrum.

21 Claims, No Drawings

MACROMER COMPOSITION INCLUDING LIGHT ACTIVATED INITIATOR

CROSS-REFERENCE TO RELATED APPLICATIONS

The present non-provisional Application claims the benefit of provisional Application having Ser. No. 60/690,706 filed on Jun. 15, 2005, and entitled MACROMER COMPOSITION INCLUDING VISIBLE LIGHT ACTIVATED INITIATORS.

FIELD OF THE INVENTION

The present invention relates to polymerizable compositions that include water-soluble light-activated polymerization initiators, and methods for in situ matrix formation using the polymerizable compositions. The invention also relates to methods for improving or restoring tissue function using the in situ formed matrices.

BACKGROUND OF THE INVENTION

Thixotropic polymerizable composites that are light curable and that contain polymerizable organic monomeric materials combined with inorganic fillers are commonly used as materials in restorative and prosthetic dental procedures. These dental materials are generally blends of polymerizable organic monomeric materials, inorganic fillers (the inorganic fillers providing structural reinforcement for the composite), and a photoinitiating system that includes a photoinitiator and photoreducers such as tertiary amines. More specifically, these dental compositions typically include a mixture of acrylate-based polymerizable monomeric materials such as methyl methacrylate, particulate fillers such as hydroxyapatite, camphorquinone as a photoinitiator, and tertiary amines as polymerization cofactors. These mixtures are non-aqueous and have like a paste-like consistency until they are hardened by polymerization.

In performing these dental procedures, these polymerizable composites are typically applied to a target area in the oral cavity, where the polymerizable composites is needed, and then shaped or combined with a dental prosthetic that is to be bonded to a dental target. When the procedure advances to a point where the polymerizable composite can be cured, a light source is introduced and the polymerizable composite is irradiated to activate the camphorquinone photoinitiator, which absorbs light and is promoted to an excited state. The activated photoinitiators can interact with photoreducers to initiate free radical addition polymerization of the monomeric materials in the dental composites, thereby promoting the hardening of the composite. The mixture typically hardens relatively rapidly, in about 20-60 seconds.

Because of the widespread use of visible light activated photoinitiators such as camphorquinone in polymerizable dental composites, lamps specifically useful for promoting the activation of this molecule for hardening the mixtures are commonly found in places where dental procedures are carried out. Since camphorquinone optimally absorbs, and is activated by light in range of about 440 nm to 500 nm (with a maximum absorbance of about 470 nm), lamps or other light sources having this emission spectrum are preferably used. Although argon-ion lasers can be used to activate photoinitiators such as camphorquinone, plasma arc, conventional halogen lamps, fast halogen lamps, and more commonly LED (light emitting diode) sources are used as activating light sources. LED sources can emit radiation over a narrow spectrum coincident with the maximum absorbance of camphorquinone, and generally do not produce excessive heat. It is noted that the photoinitiation mechanism that is provided by a camphorquinone/LED system is relatively weak as compared to photoinitiation systems that use short wavelength UV (e.g., UVA) activated photoinitiators in conjunction with high intensity low-UV emitting light sources, such as metal halide bulbs.

The polymerization of materials in dental composites is generally improved by the physical properties of a thixotropic composition, and the presence of ancillary agents, such as photoreducers or accelerants. Given this, polymerizable compositions that are non-thixotropic (for example, aqueous compositions) are not commonly used for dental procedures.

While the physical properties of thixotropic compositions are particularly amenable to dental procedures, the chemical characteristics of these compositions may be less than desirable. Some small molecular weight compounds present in dental compositions, such as monomeric materials and ancillary reagents, may present toxicity concerns. If not completely consumed in the polymerization reaction, these monomeric materials may leach out of the composite. Furthermore, the solvent systems used in thixotropic compositions, especially those having an organic component, may be less than ideal for oral use.

While thixotropic compositions are commonly used for restorative and prosthetic dental procedures, these compositions are generally not used for the treatment of degeneration of hard tissue such as bone, or softer tissue such as cartilage. Such degenerative conditions are often seen in periodontitis, which is a chronic infective disease of the gums caused by bacteria present in dental plaque. This condition induces the breakdown of the tooth supporting apparatus until teeth are lost. Surgery may be indicated to arrest disease progression and regenerate lost tissues. Several surgical techniques have been developed to regenerate periodontal tissues including guided tissue regeneration (GTR), bone grafting (BG) and the use of enamel matrix derivative (EMD).

The present invention relates to novel polymerizable systems and methods that can be used to address challenges associated with tissue regeneration. While the inventive compositions and methods described herein are particularly useful for dental purposes, they can also be used to treat other medical conditions.

SUMMARY OF THE INVENTION

Generally, the present invention relates to compositions and methods for forming matrices from compositions that include a macromer and a water-soluble polymerization photoinitiator that is activated by visible light.

In some aspects, the matrix-forming compositions are used in methods for the in situ treatment of a medical condition or indication. Such treatment can include restoring, improving, and/or augmenting tissue growth or function. The inventive compositions described herein can be used to form a matrix of polymerized macromers in contact with a host tissue. The matrix can restore or improve tissue growth or function by, for example, promoting or permitting formation of new tissue between and into the matrix. The effect on tissue can be caused by the macromer itself, or the macromer in combination with one or more bioactive agent(s) that can be present in and/or released from the matrix.

Generally, the present invention provides a matrix-forming composition that includes a water-soluble visible light-activated polymerization initiator and a macromer, which are used in conjunction with a visible light-emitting source. The visible-light emitting source has a peak wavelength that is greater than 400 nm, and generally greater than 430 nm. The visible-light emitting source can be selected from plasma arc, conventional halogen lamps, fast halogen lamps, and LEDs. A preferred source is a LED. The visible-light emitting source has a spectral output that can activate the photoinitiator, thereby promoting polymerization of the macromers component and formation of the matrix.

The present inventive compositions and methods are advantageous from the standpoint that visible-light emitting sources, such as LEDs and halogen lamps, are commonly used in many dental and medical processes, and/or are commercially available. In addition, these types of light sources are generally safe when used in connection with biological tissue. That is, the spectral output emitted from these light sources is primarily within the visible light spectrum which minimizes damage to tissue, including damage to nucleic acids of living cells. Given this, in some aspects, the inventive compositions can be used with commonly available dental equipment to treat conditions that affect hard tissue such as bone, or softer tissue such as cartilage.

The use of a visible light activated photointiators and visible light sources (for example those having a peak excitation/emission wavelength of about 400 nm or greater), in conjunction with a macromer in a water soluble composition can be technically challenging. Visible light activated photoinitiators provide a relatively weak mechanism for propagating free radical polymerization within a solution. Typically, these types of photoinitiators are utilized in a polymerization system along with various ancillary co-reagents to enhance polymerization. A reducing agent, such as a tertiary amine, is a commonly used co-reagent. The tertiary amine can improve the ability of the low energy photoinitiator to generate free radical species following light activation by acting as a reducing agent, facilitating hydrogen abstraction during radical species generation.

Low molecular weight monomeric compounds can also enhance polymerization. However, for in situ use it can be desirable to reduce or eliminate the presence of certain types of low molecular weight compounds in order to improve the biocompatibility of the composition. The inventive compositions and methods overcome challenges associated with the use of this photoinitiation system in a non-thixotropic composition.

Based on the advances described herein, the present invention provides a matrix-forming composition that includes a water-soluble photoinitiator and a macromer, the composition capable of being polymerized into a matrix when exposed to a visible-light emitting source, such as one having a peak wavelength that about 400 nm or greater. In some aspects of the invention, these matrix-forming compositions can be prepared without requiring the presence of a plurality of ancillary agents (such as multiple low molecular weight monomeric compounds or co-initiators which may present safety concerns) to promote polymerization of the composition. Upon irradiation, the inventive compositions provide a well-formed matrix having elastomeric properties that are particularly suitable for in situ applications.

Therefore, in one aspect, the invention provides a method for forming a matrix in situ. The method includes the steps of (a) providing a matrix-forming composition to a surface, the composition including a (i) macromer and (ii) a water-soluble visible light activated photoinitiator having an activation wavelength of 400 nm or greater, and (b) activating the photoinitiator to promote formation of the matrix with a LED source having a peak emission wavelength of greater than 400 nm. In some preferred embodiments the water-soluble photoinitiator has an activation wavelength in the range of about 440 to 500 nm. An exemplary method includes providing a composition that includes camphorquinone and then activating the composition with an LED source.

In another aspect, the invention relates to processes for restoring or improving tissue growth or function in a dental procedure. For example, the steps of the process can be performed to create a polymerized matrix of material in a periodontal procedure. The process can include the steps of (a) applying a matrix-forming periodontal composition to a tissue in the oral cavity, the composition comprising (i) a macromer and (ii) a water-soluble photoinitiator having an activation wavelength of 400 nm or greater; (b) treating the composition with light to activate the photoinitiator and promote formation of a matrix. For example, the composition may be applied along the gumline and irradiated to form the matrix. The polymerizable dental composition can be prepared to improve or restore tissue growth or function, and can include a bioactive agent.

In some aspects, the matrix-forming composition includes a bio-macromer. A bio-macromer refers to a polymerizable, naturally occurring polymer or naturally occurring polymer derivative. A bio-macromer is generally formed by obtaining a naturally occurring polymer or portion thereof, and derivatizing the polymer to add polymerizable groups, such as ethylenically unsaturated groups.

In yet another aspect, the invention provides a matrix-forming composition comprising (a) a bio-macromer comprising a polysaccharide, and (b) a water-soluble photoinitiator having an activation wavelength of about 400 nm or greater. In some aspects, the polysaccharide is a mucopolysaccharide. For example, the mucopolysaccharide can be selected from the group including hyaluronic acid, chondroitin acids, keratosulphates, dermatane sulphates, and heparin. An exemplary composition includes a polysaccharide bio-macromer at a concentration in the range of about 50 mg/mL to about 100 mg/mL.

In some aspects of the invention the matrix-forming composition includes both a polysaccharide macromer and a polypeptide or active portion thereof. The polypeptide may also be in the form of a macromer. One group of useful polypeptides includes those that are found in, or derived from, connective tissue, such as collagen.

In some aspects of the invention, the matrix-forming composition has a high viscosity. Preparation of a matrix forming composition that includes a viscous bio-macromer, such as hyaluronic acid, can be challenging from the standpoint that the viscosity of the solution provides an obstacle to the adequate mixing of the photoinitiator (or other ancillary reagent) in the composition. If the reagents of the composition are not well mixed, a partial or defective matrix may form, or no matrix may form at all. In these aspects, the bio-macromer can contribute in part or in whole to the highly viscous properties of the matrix-forming composition.

Therefore, in another aspect, the invention provides a matrix-forming composition comprising (a) a macromer, and (b) a water-soluble photoinitiator having an activation wavelength of about 400 nm or greater, wherein the composition has a viscosity of about 500 centi Pose (cP) or greater. In some preferred embodiments the photoinitiator has an activation wavelength in the range of about 440 to 500 nm.

Other benefits of the present invention are seen in that a matrix-forming composition can be prepared without requiring a plurality of auxiliary reagents to promote or enhance the polymerization reaction of the macromer composition. Generally, this reduces the presence of small monomeric compounds that, in some cases, may diffuse out of the formed matrix and exhibit an undesirable effect in vivo. In one aspect, it has been surprisingly discovered, that suitable matrix-formation can be obtained by including a moderately reactive, non-toxic polymerization peroxide co-initiator in the high viscosity composition.

Therefore, in another aspect, the invention provides polymerizable composition comprising a macromer, a water-soluble polymerization photoinitiator having an activation wavelength of about 400 nm or greater, and a peroxide co-initiator. The polymerization co-initiator can be selected from organic peroxides, including hydroperoxides. In preferred aspects the co-initiator includes a hydroperoxide that includes an alkyl hydroperoxide, such as para-menthane, t-butyl hydroperoxide, or t-butyl perbenzoate.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to polymerizable compositions that include macromers and photoinitiators, methods using these compositions to form matrices, the matrices that are formed from these compositions, and the use of the matrices for various applications. Exemplary embodiments illustrate the use of the matrix-forming compositions in dental procedures. However, the composition can be applied to any synthetic or natural surface and then activated to polymerize the composition. The compositions and methods of the invention can be used in various other applications, including cellular encapsulation; for adhesives, sealants, and barriers; for controlled release carriers, for tissue replacement/scaffolding, for wound dressings, and for in situ device formation. In some aspects, the polymerized matrices can form coatings on the surfaces of synthetic articles, such as implantable medical devices. Alternatively, the composition can be used to coat the surfaces of natural articles such as cells or cell-containing objects such as tissue, for example, in cell encapsulation processes.

In some aspects, the invention relates to a process for forming a matrix of polymerized material in situ. The inventive matrix-forming compositions can facilitate processes where it is desirable to treat conditions wherein tissue repair or augmentation is desired. Generally, the polymerizable composition of the invention is applied to one or more portions of the body where it is desired to form a polymerized matrix. The composition is then treated to form a matrix of polymerized material at that location. The formed matrix can serve one or more functions after formation, including tissue replacement, scaffolding, tissue augmentation, or as an adhesive or sealant.

For example, the macromer composition can be applied to a tissue and subsequently illuminated to polymerize the macromers. This results in the formation of a matrix upon which in-growing cells can migrate and organize to form tissue. For example, periodontitis can be treated by providing the composition of the present invention, in addition to a growth factor, to tissue such as bone. In some aspects, the macromer composition can include a growth factor which can be eluted or otherwise released from the matrix, and which stimulates the in-growth of desired cell types. That is, the local concentration of growth factor in the vicinity of the matrix causes migration of cells to the vicinity of the matrix, and in many cases into the matrix itself. In other aspects, the matrix provides factors that are not eluted from the matrix yet can stimulate the in-growth of desired cell types. While, in many cases, the polymerized macromer of the matrix can provide this function, other factors can be included in the matrix to supplement this function or provide a varied function. In other aspects, the matrix can include a bioactive agent that is present within the matrix and a factor that affects cell growth that is included in the matrix. In some aspects the factor is a part of the matrix.

As described herein, the macromer compositions and method of the present invention can also be used to fill the spaces between a tissue implant or preformed device and adjacent tissue. For example, the macromer compositions can be used in conjunction with tissue implants such as those from autograft, allograft or xenograft transplants, or transplants provided by tissue engineering. Current tissue engineering products often consist of cultured tissues that are implanted into tissue defects. Such products do not typically conform well to adjacent native tissue leaving spaces into which undesirable fluids and cells can accumulate and produce adverse tissue responses. For example, when cultured cartilage is implanted into cartilage defects, synovial fluid and macrophages can enter the unfilled space and lead to fibrous tissue formation, which prevents integration of the implanted cartilage with the native cartilage. Other cultured tissues that are implanted into tissue defects, and that would benefit from the matrix formed from the macromer composition of the present invention include, but are not limited to, skin, bone, ligaments, blood vessels, and heart valves.

The macromer composition and method of the present invention can also be used to coat and/or fill voids within or upon the surface of device that is implanted into a portion of the body. The matrix that is formed can be used to promote tissue integration into the portions of the device having the coated matrix. For example, the bio-macromer composition can be used to form a matrix on joint implants (e.g., for hip or knee reconstruction), dental implants, soft tissue cosmetic prostheses (e.g., breast implants), wound dressings, vascular prostheses (e.g., vascular grafts and stents), and ophthalmic prostheses (e.g., intracorneal lenses).

In some aspects the macromer composition can be used as a dermal filler. For example, the composition can be used in soft tissue augmentation to treat contour defects that can result from disease, tissue trauma, scarification, damage from light, and the effects of aging.

For tissue repair, the matrix can be formed to treat various tissue injuries such as chronic ulcera, decubitus wounds and pressure sores, foot ulcers, corneal injuries, tympanic membrane perforations, surgical wounds, skin graft donor sites, burn wounds, etc.

The polymerizable compositions can be polymerized into matrices that strongly adhere to natural tissues. Generally, the matrices can be formed to restore, improve, and/or augment tissue growth or function. In some aspects, the matrices can act as hemostatic barriers that can withstand the hemostatic pressures of bleeding. If a biodegradable macromer is used to form the matrix, after a period of time, such as after a suitable amount of tissue healing has taken place, the matrices are biodegraded and bioresorbed.

In an exemplary aspect of the invention, the compositions are particularly useful for tissue augmentation. In this aspect, the bio-macromer composition is applied to a target site in an unpolymerized form, and then polymerized in situ to provide a matrix of polymerized materials.

While the compositions of the present invention can be used for any sort of medical procedure, some more specific applications involves use in dental procedures. The compositions of the invention are particularly suitable for dental procedures because they can be used along with equipment and reagents that are commonly available in dental offices where procedures utilizing camphoquinone-containing mixtures are performed. Such equipment includes lamps that are used to initiate the photopolymerization of the thixotropic mixtures. In this regard, the compositions of the invention are advantageously used because the activation systems such as halogen lamps and LEDs are typically in possession of the user. Photoinitiators that have activation wavelengths in the same range as camphorquinone can also be used in the compositions and methods of the invention.

In its simplest form, the compositions of the invention include at least two components. The first component of the composition is a macromer; the second component of the composition is a photoinitiator. The photoinitiator of the inventive composition is a photoinitiator having an absorbance maximum about 400 nm or greater. In some aspects of the invention, the water-soluble polymerization initiators has a maximum absorbance in the range of about 440 to 500 nm. Examples of photoinitiators that have activation energies in these ranges include compounds such as camphorquinone, and water-soluble derivatives thereof.

Visible light can be applied to the composition in an amount sufficient to promote formation of a matrix of polymerized macromers. Other components can be present in the composition. These can be components that improve formation of the polymerized matrix, components that change or improve physical properties of the polymerized matrix, and components that can provide a therapeutic function, such as bioactive agents. If additional components are present in the composition, they can be chosen by the user to provide the matrix-forming composition and/or matrix with a desired functionality or property.

A "water soluble" photoinitiator has a solubility in the macromer composition of about 0.5% or greater.

In some embodiments, a water-soluble derivative of camphorquinone is utilized. Camphor or camphorquinone can be derivatized by techniques known in the art to add, for example, charged groups. See, for example, G. Ullrich et al. (2003) *Synthesis and photoactivity of new camphorquinone derivatives*"; Austrian Polymer Meeting 21, International H. F. Mark-Symposium, 131.

In some aspects of the invention, the water soluble photointiator is a diketone, which can be selected from water-soluble derivatives of camphoroquinone, 9,10-phenanthrenequinone, and naphthoquinone having an absorbance of 400 nm and greater. In some aspects of the invention, for example, the photoinitiator is a water-soluble non-aromatic alpha diketones, selected from water-soluble derivatives of camphorquinone.

Other suitable long-wave ultra violet (LWUV) or light-activatable molecules include, but are not limited to, [(9-oxo-2-thioxanthanyl)-oxy]acetic acid, 2-hydroxythioxanthone, and vinyloxymethylbenzoin methyl ether. Suitable visible light activatable molecules include, but are not limited to water soluble forms of initiators comprising acridine orange, ethyl eosin, eosin Y, Eosin B, erythrosine, fluorescein, methylene green, methylene blue, phloxime, riboflavin, rose bengal, thionine, xanthine dyes, and the like.

The photoinitiator having an activation wavelength of about 400 nm or greater is also present in the composition at a concentration sufficient for matrix formation. In some aspects, the water soluble photoinitiator (for example, a water-soluble non-aromatic alpha diketones such as a water-soluble camphorquinone derivative) is used at concentration about 10 mg/mL or greater. A preferred matrix-forming composition includes a water-soluble photoinitiator having an activation wavelength of about 400 nm or greater, at concentration in the range of about 10 mg/mL to 20 mg/mL.

As demonstrated by the present invention, concentrations about 10 mg/mL or greater, such as in the range of about 10 mg/mL to 20 mg/mL, have yielded particularly robust matrix forming compositions used in conjunction with a visible light emitting source having a peak wavelength of greater than 400 nm, such as an LED light source.

An exemplary matrix-forming composition includes a water-soluble camphorquinone derivative, such as camphorquinone-10-sulfonic acid, at a concentration of about 15 mg/mL.

The term "macromer" refers to a polymer having one, or two, or more than two polymerizable groups. The polymeric portion of the macromer can be a homopolymer or a copolymer, and can be natural or synthetic. It is understood that when a polymerizable group is added to the natural polymer to create a macromer, the macromer may be considered a derivative of a natural polymer. The matrix-forming composition can include one type of macromer, or a combination of different types of macromers.

In some aspects of the invention, the macromer is a naturally occurring polysaccharide. Naturally occurring polysaccharides include polysaccharide and/or polysaccharide derivatives that are obtained from natural sources, including plants, animals, and microorganisms. The naturally occurring polysaccharide can be a homoglycan or a heteroglycan; exemplary heteroglycans include diheteroglycans and triheteroglycans.

Exemplary naturally occurring polysaccharides include amylose, maltodextrin, amylopectin, starch, dextran, hyaluronic acid, heparin, chondroitin sulfate, dermatan sulfate, heparan sulfate, keratan sulfate, dextran sulfate, pentosan polysulfate, and chitosan. The naturally occurring polysaccharide can also be enzymatically degraded, but offers the advantage of being generally non-enzymatically hydrolytically stable.

In some aspects of the invention the matrix-forming composition includes macromer prepared from a plant-derived polysaccharide, such as amylose, maltodextrin, amylopectin, starch, dextran, dextran sulfate, pentosan polysulfate, or chitosan. In some aspects the plant-derived polysaccharide is a low molecular weight polymer having little or no branching, such as those that are derived from and/or found in starch preparations, for example, amylose and maltodextrin. A preferred macromer comprises a low molecular weight biodegradable polymer comprising glucopyranose units that are joined by $\alpha$-1,4 linkages. Therefore, the plant-derived polysaccharide can be a substantially non-branched or non-branched poly(glucopyranose) polymer.

Exemplary plant-derived macromers include amylose and maltodextrin macromers, the preparation of which is described in commonly assigned U.S. Pub. No. 2005/0255142A1, and U.S. patent application Ser. No. 11/271,238, filed Nov. 11, 2005. In some modes of practice a biodegradable polysaccharide macromer (such as amylose or maltodextrin) having an average molecular weight in the range of about 1000 Da to about 10,000 Da is used in combination with a photoinitiator having an activation wavelength of about 400 nm or greater, such as water soluble camphorquinone, to form a matrix in situ.

Use of this type of biodegradable macromer (for example, a maltodextrin macromer) for matrix formation can provide advantages for dental procedures. Degradation of the matrix can commence when placed in contact with saliva, which contains amylase capable of degrading the matrix. Since the matrix can be highly crosslinked, the rate of degradation can be prolonged. Furthermore, degradation of the matrix will occur by surface erosion, rather than by bulk erosion. This maintains the integrity of the matrix during its degradation. Matrices formed from these macromers can be useful for delivering a bioactive agent from the matrix over a longer period of time. The matrix is particularly suitable for the delivery of larger hydrophilic bioactive agents, such as polypeptides, nucleic acids, and polysaccharides.

In some aspects of the invention the matrix forming composition has a high viscosity. Highly viscous properties of the composition can be provided by the properties of one or more components in the composition, for example, by the macromer component. In many cases, mucopolysaccharide-based macromers provide the matrix-forming composition with highly viscous properties. Other non-mucopolysaccharide-based macromers such as carboxy methyl cellulose and carboxy methyl dextran can be included to provide highly viscous matrix-forming compositions.

Viscosity is commonly measured in units Poise (P) or centipoise (cP), or Pascal/second (Pa s$^{-1}$) using equipment such as a rotating spindle instrument, such as a Brookfield viscometer (Brookfield Engineering Laboratories, Middleboro, Mass.). The amount of force that is needed to turn the spindle (torque) is recorded in Poise (P) or centipoise (cP) (1.0 P=0.1 Newton-seconds/m$^2$). The glass capillary viscometer is the standard instrument for measuring viscosity of Newtonian fluids and is calibrated with reference to the defined value of the viscosity of water.

Factors that can affect the viscosity of the matrix-forming compositions of the invention include the concentration of polymerizable material (macromer) in the composition, the pH of the composition, the temperature of the composition, and ionic conditions of the composition. In order to demonstrate some aspects of the invention, a "high viscosity" composition is herein exemplified by referring to particular parameters of the composition. That is, a "high viscosity" composition refers to the viscosity of a composition at a selected concentration of macromer component, at a selected pH, and at a selected temperature. Any polymerizable composition that includes a macromer can be prepared, wherein the macromer is present at a selected concentration, and wherein the composition is also prepared to have a selected pH. The viscosity of the composition can then be measured at a selected temperature.

Exemplary selected parameters for determining the viscosity of a polymerizable composition are as follows.
  Concentration of macromer component(s): 5% (w/v) (e.g., 5 g of lyophilized macromer(s) per 100 mL aqueous solution)
  pH of composition: 7
  temperature: 25° C.

The viscosity of a polymeric solution, such as a polysaccharide-based solution, is thought at least to be due to the presence of a hydrogen bonded network in between and among the polymers. Factors that disrupt hydrogen bonding may contribute to a decrease in viscosity, whereas factors that promote hydrogen bonding (such as pH conditions) may lead to an increase in viscosity. Therefore, in determining the viscosity of a polymerizable composition that include macromers such as polysaccharides, it is desirable to avoid pH conditions, in particular, the isoelectric point of the macromer, that will result in the formation of a composition having an extremely high viscosity that is not representative of the viscosity of the composition over a wider pH range.

For example, it is known that mucopolysaccharides such as hyaluronic acid can be dissolved to form high viscosity aqueous solutions. The viscosity of an HA solution can vary according to the pH condition of the solution. Also, the viscosity can be significantly affected by the concentration of the macromer in solution. Small increases or decreases in the concentration of the polysaccharide can significantly increase or decrease the viscosity of solution, respectively.

Some aspects of the invention involve (a) applying a matrix-forming composition to portion of a subject, the matrix-forming composition comprising (i) a macromer and (ii) a water-soluble photoinitiator having an activation wavelength of about 400 nm or greater, wherein the composition has a viscosity of 500 cP or greater; and (b) treating the composition with light to activate the photoinitator and promote formation of a matrix comprising the macromer on the tissue.

More specifically, the steps can be performed in a dental procedure. For example, the process includes the steps of (a) applying a matrix-forming dental composition to a tissue in the oral cavity, the comprising (i) a macromer and (ii) a photoinitiator having an activation wavelength of about 400 nm or greater, wherein the polymerizable dental composition has a viscosity of about 500 cP or greater; (b) treating the composition with light to activate the photoinitator and promote formation of a hydrogel comprising the macromer on the tissue.

Mucopolysaccharides, which are also known as glycosaminoglycans, are negatively charged polymers that can be included in the inventive compositions described herein in macromer form to form highly viscous matrix-forming compositions. Suitable mucopolysaccharides contemplated by the invention include those that are found in the lubricating fluid of the joints and as components of cartilage, synovial fluid, vitreous humor, bone, and heart valves. Typical mucopolysaccharides are long and unbranched polymers. However these polymers can be modified to affect the branching and length of the polymers, for example, if a shorter and/or less branched mucopolysaccharides desired. Mucopolycaccharides typically include repeating disaccharide units that contain either of two amino sugar compounds, for example, N-acetylgalactosamine or N-acetylglucosamine, and an uronic acid such as glucuronate. Exemplary naturally occurring mucopolysaccharides which can be included in the polymerizable composition include, for example, hyaluronic acid, dermatan sulfate, chondroitin sulfate, heparin, heparan sulfate, and keratan sulfate.

In some aspects of the invention a bio-macromer composition that includes mucopolysaccharides can be used if a patient displays sensitivity to a polypeptide based bio-macromer, such as collagen (for example, bovine collagen). In other aspects it may be desired to utilize a mucopolysaccharide-based composition to avoid the use of animal-derived material.

Hyaluronic acid is a nonadhesive (to proteins), nonimmunogenic, and naturally derived linear polymer that includes alternating β1,4-glucuronic acid and β1,3-N-acetyl-D-glucosamine units. HA is the principal glycosaminoglycan in connective tissue fluids. Commercially available preparations of HA (such as HA Na+ salt) can be used to prepare the macromer. Has having a molecular weight in the range of $1\times10^5$–$2\times10^6$ can be used.

In addition to its role providing a structural function in the extracellular matrix, HA is also thought to effect cellular function by controlling macro- and microenvironments of tissue, as well as through direct receptor mediated effects on gene expression. HA is thought to exert this effect via its binding to extracellular matrix molecules and cell surface receptors. Cells such as keratinocytes, fibroblasts, and chondrocytes can be affected by the presence of HA. HA is thought to promote wound healing by promoting early stages of inflammation, but regulating later stages of inflammation.

Any sort of water-soluble HA polymer or water-soluble HA polymer derivative can be used as a macromer component in the present invention. Water-soluble esterified derivatives of HA, such as HAs having partial esterification, can be included in the matrix forming composition. For example, derivatives of HA such as benzyl esters of HA (Italiano, G. et al. (1997) *Urol. Res.*, 25(2):137-42) can be used as macromers in the present matrix-forming compositions. In other aspects, low molecular weight fragments of HA (Chen and Abatangelo (1999) *Wound Repair Regen.*, 7:79-89) can be used as macromers in the present matrix-forming compositions. Low molecular weight fragments of HAs have been shown to promote agiogenesis and endothelial cell proliferation (West and Kumar (1989) Exp. Cell. Res., 183:179-196). HA can be fragmented in the presence of hyaluronidase.

Hyaluronic acid can be obtained from eukaryotic sources such as bovine vitreous humor, rooster combs, or umbilical cords, and also can be obtained from bacterial sources such as *Streptococcus zooepidemicus*. Depending on the desired use for a polymerizable composition that includes HA, one or more of these sources can be used for the preparation of the composition.

Chondroitin sulphate is a polymer of N-acetylgalactosamine-glucuronic acid disaccharides. Chondroitin sulphate can be found in tissues and fluids such as cartilage, synovium, and synovial fluid. Various sulphated forms of chondroitin, such as those having various sufation patterns, for example various C4S:C6S ratios (chondroitin-4-sulphate, C4S, or chondroitin sulphate A; chondroitin-6-sulphate, C6S, or chondroitin sulphate C) can be used in the matrix-forming compositions of the present invention.

Polypeptides constitute another class of polymers than can be used in the present invention to form macromers. As used herein, the term "polypeptide" is used in its broadest sense and refers to a polymer that includes two or more naturally occurring and/or synthetic amino acid residues. More specific types of polypeptides include peptides, for example, relatively short polypeptides that have less than 40, 30, or 20 amino acids, and proteins, which generally refer to larger polypeptides. Any sort of naturally occurring, synthetic, recombinant, or derivatized protein can be used as a macromer component in the matrix-forming composition of the present invention.

The polypeptide macromer can have properties that can affect tissue that is in contact with the matrix. Various types of polypeptides macromers can form matrices that can improve tissue function or promote tissue growth. Other polypeptides macromers can be used to provide a structural function to matrix, and can also be compatible with the tissue they are in contact with. Examples of polypeptides that can be suitably used to form macromers include collagen, albumin, elastin, fibronectin, vitronectin, laminin, casein, various globulins, etc., and their biologically acceptable synthetic derivatives.

One group of useful polypeptides includes those that are found in, or derived from, connective tissue.

One type of particularly useful polypeptide is gelatin. Gelatin is a denatured form of the connective tissue protein collagen. Several types of gelatin can be prepared or commercially obtained. Gelatin can be prepared from collagen that is obtained from a variety of sources. The extraction and production process employed can also yield various collagen/gelatin preparations. Any suitable gelatin preparation can be used to form a gelatin macromer. Suitable types of gelatin include those that are extracted from animal bones and from animal skin. Usually, the animal material is from bovine or porcine origin. Depending on the extraction process, two types of gelatin can be prepared: the A (or acidic) type, which is prepared by acid hydrolysis of the collagen and which has an isoelectric point of about 8, and the B (or basic) type, which is prepared by basic hydrolysis of the collagen and which has an isoelectric point of about 5.

In some aspects, the composition can include a blend of two or more different macromers. For example, the blend may include a mucopolysaccharide macromer (such as an HA macromer) and one or more other macromers that can be selected from mucopolysaccharide macromers, polypeptide macromers, or synthetic macromers. In other examples, the blend may include a polypeptide macromer and one or more other macromers that can be selected from mucopolysaccharide macromers, polypeptide macromers, or synthetic macromers. In one aspect of the invention the matrix-forming composition includes a mixture of a mucopolysaccharide macromer and a polypeptide macromer, for example a polypeptide macromer that is derived from connective tissue such as collagen or gelatin. One exemplary mixture include a HA macromer and a collagen macromer.

Therefore a composition of the invention can include (a) a bio-macromer comprising a mucopolysaccharide, (b) a bio-macromer comprising a polypeptide, and (c) a water-soluble photoinitiator having an activation wavelength of about 400 nm or greater.

Macromers derived from non-natural polymers, such as those that have synthetic polymer backbones, can be included in the matrix-forming composition. The non-natural macromers may change and/or improve properties of the matrix formed following polymerization of the macromer composition to form the matrix. For example, a non-natural macromer when used to form the matrix may reduce the biodegradablility of the matrix. Non-natural macromers macromers include, but are not limited to, polymerizable poly(vinylpyrrolidone) (PVP), poly(ethylene glycol) (PEG), poly(ethylene oxide), poly(ethyloxazoline), poly(propylene oxide), polyacrylamide (PAA), poly(vinyl alcohol) (PVA), copolymers thereof, and the like. These types of macromers are typically soluble in water and are more stable in vivo as compared to biodegradable polymers.

Non-natural water-soluble biodegradable macromers, such as those that have synthetic and biodegradable polymer backbones can also be included in the polymerizable composition. Exemplary non-natural water-soluble biodegradable macromers can include PEG portions with biodegradable lactide linkages and terminal acrylate groups.

The matrix-forming composition can be prepared by dissolving or suspending the macromer component and the polymerization initiator in a suitable solution, such as an aqueous solution. If the macromer does not dissolve readily in the solution, it may be desirable to first dissolve the macromer before adding other components to the solution. For example, the macromer components is obtained dissolved or suspended in solution and then the water-soluble polymerization initiator is added to the solution, along with other ancillary components, if desired, to prepare the matrix-forming composition.

The matrix-forming composition can include an amount of macromer, or a combination of macromers, in an amount that provides the matrix with desired properties. For example, the amount of macromer in the matrix-forming composition can be adjusted to change the strength, elasticity, and/or porosity of the formed matrix. For example, for in situ use, the amount of macromer(s) can provide the matrix with sufficient strength and elastomeric properties suitable for oral application.

Generally, the macromer, such as a bio-macromer, is present in the composition at a concentration sufficient for matrix formation. The polymerizable material can include one or more bio-macromers, or a combination of one or more bio-macromers and a non-macromer polymerizable material. In some embodiments, the polymerizable material (that is, the total of all macromer(s) components and, if present, any non-macromer components in the composition) is in an amount of about 50 mg/mL or greater in the composition. In some aspects, the macromer component (for example, a polymucosaccharide macromer such as an HA macromer), is present in an amount of about 50 mg/mL or greater. An exemplary range is from about 50 mg/mL to about 125 mg/mL, and more specifically in the range of about 50 mg/mL to about 100 mg/mL. A macromer concentration in this range provides the added benefits of ease of composition preparation. An exemplary polymerizable composition includes an HA macromer at a concentration of about 75 mg/mL. In some aspects, if the biomacromer contributes to the high viscosity of the composition, it is preferred that the concentration of the bio-macromer in the composition is up to about 100 mg/mL.

As used herein, the term "polymerizable group" will generally refer to a group that is polymerizable in the presence of free radicals formed by activation the water-soluble photoinitiator upon exposure to light at a wavelength of about 400 nm or greater. Polymerizable groups generally include a carbon-carbon double bond and can be ethylenically unsaturated or vinyl groups. Exemplary polymerizable groups include acrylate groups, methacrylate groups, ethacrylate groups, 2-phenyl acrylate groups, acrylamide groups, methacrylamide groups, itaconate groups, and styrene groups.

Polymers, such as polysaccharides and polypeptides, can be effectively derivatized in organic, polar, or anhydrous solvents, or solvent combinations to produce polysaccharide or polypeptide-based macromers. Generally, a solvent system is used that allows for polymer solubility and control over the derivatization with polymerizable groups. A particularly useful solvent for polymer derivatization is formamide. Other solvents or solvent combinations may be used.

Macromer preparation (addition of polymerizable groups to the polymer) can be carried out using any suitable method. Polymerizable groups such as glycidyl acrylate can be added to polysaccharides and polypeptides in straightforward synthetic processes. In some aspects, the polymerizable group is present on the bio-macromer at a molar ratio of 0.05 µmol or greater of polymerizable group (such as an acrylate group) per 1 mg of macromer. In some aspects the macromer is derivatized with polymerizable groups in amount in the range from about 0.05 µmol to about 2 µmol of polymerizable group (such as an acrylate group) per 1 mg of macromer.

For example, hyaluronic acid can be reacted with a compound containing a polymerizable group, such as glycidyl acrylate, in the presence of formamide (and TEA, for pH control) to provide acrylate-derivatized hyaluronic acid molecules. The number and/or density of acrylate groups can be controlled using the present method, e.g., by controlling the relative concentration of reactive moiety to saccharide group content.

In another example, polymerizable groups can be added to collagen via reaction of amine containing lysine residues with acryloyl chloride. Collagen can be dissolved in formamide with the addition of acryloyl chloride (and TEA, for pH control) to provide acrylate-derivatized collagen molecules.

Crosslinker chemistry can also be used to add polymerizable groups to a naturally occurring polymer. For example, proteins such as collagen or gelatin can be with derivatized with varying amounts of vinyl containing compounds such as vinylbenzoic acid. Neutralized solutions of gelatin and vinylbenzoic acid can be mixed in the cold followed by the addition of a crosslinker such as 1-ethyl-3-(3-dimethylaminopropyl) carbodiimide.

The macromer can be subject to purification, for example, by dialysis, before use in the matrix-forming composition.

In some aspects of the invention, the matrix-forming composition includes (a) a bio-macromer having 0.05 µmol or greater of polymerizable group (such as an acrylate group) per 1 mg of macromer and (b) a water-soluble photoinitiator having an activation wavelength of about 400 nm or greater. An exemplary bio-macromer is hyaluronic acid having about 0.2 µmol of acrylate group per 1 mg of hyaluronic acid.

Other non-polymerizable natural or synthetic materials can optionally be included in the macromer composition. For example, any mucopolysaccharide, polypeptide, synthetic polymer or biodegradable polymer, such as those described herein although in non-macromer form, can be included in the macromer composition. A non-derivatized polymer (i.e., non-derivatized with a polymerizable group) that serves as a plasticizing agent can be added to the matrix-forming composition.

The matrix-forming composition of the present invention can include one or more other components that are different than the bio-macromer and the water-soluble polymerization initiator. A strong elastomeric matrix can be formed in the presence of one, or more than one ancillary reagent(s). However, in some aspects, it has been found that a plurality of ancillary reagents are not required to provide suitable matrix formation. This can be a benefit in the preparation and use of polymerizable compositions as this can reduces the presence of these types of compounds that, in some cases, may diffuse out of the formed matrix and exhibit an undesirable effect in vivo.

Given this, the co-initiator system can be a unary system, meaning that only one primary component is required to enhance polymerization in a manner sufficient for matrix formation. A unary system has a predominant component; other components can be present in amounts that provide no significant effect to the matrix forming process, or the predominant component may be the only component in the co-initiator system.

According to one aspect of the invention, it has been surprisingly discovered that good matrix-formation can be obtained by including a stable (i.e., not highly reactive), non-toxic peroxide polymerization co-initiator in the matrix-forming composition.

Therefore, in another aspect of the invention, the composition includes a bio-macromer, a water-soluble photoinitiator having an absorbance of about 400 nm and greater, and a peroxide polymerization co-initiator. In some aspects the oxidizing polymerization co-initiator is an organic peroxide that is a derivative of hydrogen peroxides ($H_2O_2$) in which one or both of the hydrogen atoms are replaced by an organic group. Organic peroxides contain the —O—O— bond within the molecular structure, and the chemical properties of the peroxides originate from this bond.

Various types of organic peroxides can be used. While highly reactive organic peroxides that can undergo self-accelerating thermal decomposition below room temperature can be used, it is generally more desirable to use stable organic peroxides that decompose in the presence of an activating agent such as an initiator. Stable organic peroxides generally decompose upon heating to high temperatures (60° C.), although processes that involve heating to high temperatures are generally not performed during in situ polymerization processes.

In some aspects of the invention, the peroxide polymerization co-initiator is a stable organic peroxide, such as an alkyl hydroperoxide.

A polymerization co-initiator can be selected from, for example, diacyl peroxides, peroxyesters, dialkyl peroxides, peroxyketals, ketone peroxides, hydroperoxides. The diacyl peroxides include benzoyl peroxide, 2,4-dichlorobenzoyl peroxide, m-toluoyl peroxide, lauroyl peroxide, and dibenzoyl peroxide. The peroxyesters include, for example, t-butylperoxy benzoate, bis-t-butylperoxy isophthalate, 2,5-dimethyl-2,5-bis(benzoylperoxy)hexane, t-butylperoxy 2-ethylhexanoate, and t-butylperoxyisopropyl carbonate. The dialkyl peroxides include, for example, dicumyl peroxide, di-t-butyl peroxide, diisopropyl peroxide, and dilauryl peroxide. The peroxyketals include, for example, 1,1-bis(t-butylperoxy)-3,3,5-trimethylcyclohexane, 1,1-bis(t-butylperoxy)cyclohexane, and 1,1-bis(t-hexylperoxy)cyclohexane. The ketone peroxides include, for example, methyl ethyl ketone peroxide, cyclohexanone peroxide, and methyl acetocetate peroxide. The hydroperoxides include, for example, t-butyl hydroperoxide, cumene hydroperoxide, and p-diisopropylbenzene peroxide.

In some aspects the co-initiator includes a hydroperoxide that includes an alkyl hydroperoxide, such as para-menthane hydroperoxide, t-butyl hydroperoxide, p-diisopropylbenzene peroxide, cumene hydroperoxide, acetyl peroxide, t-amyl hydrogen peroxide, and cumyl hydrogen peroxide.

Other polymerization co-initiators include 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, 2,5-dimethyl-2,5-di-t-butylperoxyhexane, 2,5-dimethyl-2,5-di-t-butyl-peroxyhex-3-yne, and 4-methyl-2,2-di-t-butylperoxypentane.

The polymerization co-initiator can be present in the composition at a concentration sufficient for matrix formation. In some aspects the polymerization co-initiator is present in the composition at concentration of about 7 mg/mL or greater; for example the polymerization co-initiator is present in the range of about 7 mg/mL to about 14 mg/mL. In some aspects, the polymerization co-initiator is a hydroperoxide or peroxide, for example, an alkyl peroxide such as t-butyl hydroperoxide present in the bio-macromer composition in the range of about 7 mg/mL to about 14 mg/mL.

Other polymerization co-initiators include azo compounds such as 2-azobis(isobutyro-nitrile), ammonium persulfate, and potassium persulfate.

In some aspects, the composition that includes the macromer, polymerization initiator, and polymerization co-initiator can also include one or more other reagent(s), such as reducing agents, and/or polymerization accelerants. The reducing agents or polymerization accelerants can include, but are not limited to, any of those described herein. Also, the reducing agents or polymerization accelerants can be included in the composition at any useful concentration.

In some aspects of the invention, the matrix-forming composition can include a reducing agent such as a tertiary amine. For example, the composition can include (a) a macromer, such as a biomacromer, (b) a water-soluble photoinitiator having an activation wavelength of about 400 nm or greater, and (c) a tertiary amine. In some aspects the matrix-forming composition has a viscosity of about 500 cP or greater. In many cases the reducing agent, such as a tertiary amine, can improve free radical generation.

Examples of the amine compound include primary amines such as n-butylamine, n-hexylamine, n-octylamine and aniline; secondary amines such as N-methylaniline, N-methyl-p-toluidine, dibutylamine and diphenylamine; aliphatic tertiary amines such as triethylamine, tributylamine, tripropylamine, N,N'-dimethylaniline, N,N'-dibenzylaniline and N,N'-dimethylaminoethyl methacrylate, ethyldiethylaminobenzoate (EDAB) trimethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate; and aromatic tertiary amines such as p-dimethylaminobenzoic acid, amyl p-dimethylaminobenzoate, ethyl p-dimethylaminobenzoate, N,N'-dimethylanthranic acid methyl ester, p-dimethylaminophenetyl alcohol, N,N'-di(P-hydroxyethyl)-p-toluidine, N,N'-dimethyl-p-toluidine, and N,N'-diethyl-p-toluidine, N,N-dimethylaniline, N,N-dimethyl-p-toluidine, N,N-diethyl-p-toluidine, N,N-dimethyl-3,5-dimethylaniline, N,N-dimethyl-4-ethylaniline, N,N-dimethyl-4-t-butylaniline, N,N-bis(2-hydroxyethyl)p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-t-butylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate and 4-dimethylaminobenzophenone. In some particular aspects of the invention, a tertiary amine, such as an aromatic tertiary amine, is present in the matrix-forming composition.

In some aspects of the invention filler particles can be included in the matrix-forming composition. The filler particles can be used for one or more purposes, for example, to provide additional structural properties to the matrix, such as strength, and/or to provide a mechanism for forming a matrix having a bioactive agent. For example, a bioactive agent, such as a bioactive agent that is a peptide, can be bound, coupled, or adsorbed onto the filler particle.

In some aspects, the filler particle can include a surface reactive glass. Examples include borosilicate glass, soda glass; (heavy metal) e.g., barium-, strontium-, or zirconium-containing glass; aluminosilicate; fluoroaluminosilicate; glass ceramics; silica as well as composite inorganic oxides such as silica-zirconia, silica-titania and silica-alumina, ultrafine powdery silica, ultrafine alumina, ultrafine zirconia, ultrafine titania, amorphous silica, silica-titania-barium oxide, quartz and alumina.

Surface reactive glass particles are commercially available from, for example, Industrial Corporation or from Schott Glass Electronic Packaging Company. Specific examples of surface reactive glass particles are those that include fluoroaluminosilicate glass powders having an average particle size of about 0.2 to about 10 micrometers, which are capable of releasing fluorine, and comprise, based on the total weight of the glass, about 20 to about 50% by weight of $SiO_2$, about 20 to about 40% by weight of $Al_2O_3$, about 15 to about 40% by weight of BaO, and about 1 to about 20% by weight of $F_2$ as described in Published Japanese Patent Application No. 55882/1995. Surface reactive glass particles can also include a lanthanide metal element such as, for example, La, Gd, and/or Yb. In some aspects the surface reactive glass particles can release fluorine when part of a dental restoration.

Filler particles can also include irregular-shaped particles, the spherical particles, or fine particles, or combinations thereof. The filler particle can also be a polymer-based filler particle. These fillers can be used in the matrix-forming composition alone, or with other filler particles such as the surface reactive glass filler particles. Examples of other fillers include amorphous silica, aluminium silicate, aluminium oxide, aluminium nitride, aluminium sulfate, barium sulfate, boron carbide, calcium carbonate, calcium hydroxide, calcium phosphate (including ammoniated or deammoniatedi calcium phosphate, and tricalcium phosphate), calcium sulfate, clay, hydroxyapatite, kaolin, lithium silicate, lithium alumina silicate, mica, quartz, silicon carbide, silicon nitride, strontium silicate, strontium hydroxide strontium borosilicate, talc tin oxide, titanium oxide, titanium nitride, zirconium oxide, and zeolite.

In other aspects of the invention, in addition to these components, the matrix-forming composition can include one or more polymerization accelerator(s). For example, a polymerization accelerator having a biocompatible functional group (e.g., a biocompatible polymerization accelerator) is included in the matrix-forming composition of the present invention. The biocompatible polymerization accelerator can also include an N-vinyl group such as N-vinyl amide group. These types of polymerization initiators can promote matrix formation.

Exemplary biocompatible polymerization accelerators include sulfonated N-vinyl capryllactam (1-vinyl-azonan-2-one), sulfonated N-vinyl enatholactam (1-vinyl-azocan-2-one), sulfonated N-vinyl caprolactam (1-vinyl-azepan-2-one), sulfonated N-vinyl valerolactam (1-vinyl-piperidin-2-one), and sulfonated N-vinyl butyrolactam (1-vinyl-pyrrolidin-2-one), and the like; linear sulfonated N-vinyl carboxamides such as vinylcarbamoyl-methanesulfonate, 2-vinylcarbamoyl-ethanesulfonate, 3-vinylcarbamoyl-propane-1-sulfonate, 4-vinylcarbamoyl-butane-1-sulfonate, 5-vinylcarbamoyl-pentane-1-sulfonate, 6-vinylcarbamoyl-hexane-1-sulfonate, 7-vinylcarbamoyl-heptane-1-sulfonate, and the like; and also sulfonated cyclic N-vinyl imides such as sulfonated N-vinyl succinimide (sulfonated 1-vinyl-pyrrolidine-2,5-dione), sulfonated N-vinyl glutarimide (sulfonated 1-vinyl-piperidine-2,6-dione), and sulfonated N-vinyl phthalimide (sulfonate 2-vinyl-isoindole-1,3-dione) and the like. Biocompatible polymerization accelerators are described in commonly assigned U.S. Patent Application Publication No. 2005/0112086.

The polymerization accelerator can be present in the composition at a concentration sufficient to accelerate matrix formation. In some aspects the polymerization accelerator is present in the composition at concentration of about 3 mg/mL or greater; for example, the polymerization accelerator is present in the range of about 3 mg/mL to about 7 mg/mL. Other reagents such as UV absorbers can be included in the compositions. These can be useful in some instances to protect the matrix materials from UV light, if applied in an amount during the polymerization process. UV absorbers include benzophenones, benzotriazoles, and the derivatives thereof such as TINUVIN P, a benzotriazole UV absorber available from Ciba-Geigy Corporation (Ardsly, N.Y.).

Other polysaccharides and water-soluble polymers can also be included in the bio-macromer composition. For example, synthetic derivatives of the natural polysaccharides, such as carboxymethyl cellulose, various alkyl celluloses, hydroxyethylcellulose, carboxycellulose, and oxidized starch can also be used for the purpose of the invention.

In some aspects of the invention a bioactive agent can be included in the bio-macromer composition. The matrix formed from the composition can therefore include a bioactive agent which, in many aspects, can provide a local pharmacological activity in the vicinity of the formed matrix. The matrix can therefore serve as a medium for the slow or controlled release of the bioactive agent from the matrix-coated surface. For example, bioactive agents can be stably attached to, or releasably incorporated into the matrix. The bioactive agent can be subsequently released from the matrix by diffusion of the agent out of the matrix and/or by matrix degradation.

The term "bioactive agent" refers to a peptide, protein, carbohydrate, nucleic acid (such as a gene therapy agent), lipid, polysaccharide or combinations thereof, or synthetic inorganic or organic molecule, that causes a biological effect when made available in vivo to an animal. Examples of suitable gene therapy agents include (a) therapeutic nucleic acids, including antisense DNA, antisense RNA, and interference RNA, and (b) nucleic acids encoding therapeutic gene products, including plasmid DNA and viral fragments, along with associated promoters and excipients. Examples of other molecules that can be incorporated include nucleosides, nucleotides, vitamins, minerals, and steroids.

Although not limited to such, the matrices of the invention are particularly useful for delivering bioactive agents that are hydrophilic molecules, such as polypeptides (including proteins and peptides), nucleic acids (including DNA and RNA), and polysaccharides (including heparin). These bioactive agents can be adsorbed onto the filler particles described herein.

Peptides having bioactivity are one particular class of bioactive agents. Peptides that are involved in tissue repair can be incorporated into and/or coupled to the polymeric material of the matrix. Peptides that are involved in tissue repair processes include those belonging to the EGF, FGF, PDGF, TGF-β, VEGF, PD-ECGF or IGF families, and also peptides derived from bone morphogenetic protein 2, or BMP-2

In some aspects, peptides derived from extracellular matrix proteins can be used. For example, peptides derived from collagen, albumin, elastin, fibronectin, vitronectin, laminin, or casein can be included in the matrix-forming composition. For example, the P-15 peptide, which mimics the cell-binding domain of collagen, can be included in the matrix to promote dermal fibroblast attachment and proliferation.

The bioactive agent can be present in the matrix-forming composition and matrix at any useful concentration. For example, the bioactive agent, such as a peptide, can be included in the matrix forming composition in the range of about 0.1 mg/mL to about 200 mg/mL. In some cases an antiseptic such as an antibiotic, antibacterial sulfamide or peptide, chinolone, or antimycotic, can be included in the matrix to supplement the function of the matrix in tissue repair.

In order to prepare the matrix-forming compositions, the macromer is generally mixed with the water-soluble polymerization initiator to provide a composition that can be activated to provide a well-formed matrix with elastomeric properties. A well-formed matrix has physical properties that are generally consistent throughout the matrix. Exemplary matrix-forming compositions can be prepared by mixing a macromer-containing solution with a photoinitiator under conditions that allow the photoinitiator to become well dispersed in the macromer-containing solution.

The components of the matrix-forming composition can be dissolved in water alone, or, optionally, in an aqueous solution containing a mixture of water and a water-miscible organic liquid, or in an organic liquid. In some aspects an alcohol, such as ethanol, can be included in the polymerizable composition.

In some aspects the macromer solution provides a high viscosity composition. For example, a composition that includes a biomacromer, such as an HA macromer, is mixed with a water soluble photoinitiator, such as water-soluble camphorquinone, wherein the composition has a bio-macromer concentration in the range of about 50 mg/mL to about 100 mg/mL, and also a water soluble photoinitiator concentration in the range of about 10 mg/mL to about 20 mg/mL. The composition can be mixed for a predetermined amount of time, for example, for about 2 hours at 37° C. This slightly elevated temperature allows for more rapid mixing of the components; alternatively, lower temperatures (for example, room temperature) and longer mixing times can be performed. Generally, since a visible light-activated photoinitiator is utilized, the mixing is performed in the dark. If other reagents are added to the composition they can be included at the same time or after the macromer and initiator have been mixing for the predetermined amount of time. For example, in some aspects a polymerization co-initiator is added after first mixing the macromer and initiator.

The composition can be prepared and then stored for a period of time before use. Generally, storage conditions can include storage in the dark and at lower temperatures to avoid decomposition and/or activation of the material prior to use. The amount of time (shelf life) that the composition is stored before use may depend on the exact formulation of the composition. For example, compositions that include more reactive polymerization co-initiators, such as more reactive peroxides or hydrogen peroxides, may be stored for shorter periods of time.

Alternatively, components of the composition may be combined just prior to use. For example, components of the composition may be supplied individually, as in a kit, to user and then the components may be combined at some point prior to use. For example, a kit can include (a) a macromer component and (b) a water-soluble photoinitiator having an activation wavelength of about 400 nm or greater (such as water-soluble camphorquinone), in individual vials or containers. Alternatively, a kit can include (a) a macromer component, (b) a photoinitiator, and (c) a polymerization co-initiator (for example a peroxide or hydrogen peroxide co-initiator). Other reagents can also be present in the kit, such as diluents, if any one or more of the components are supplied in dry or lyophilized form. Other ancillary reagents can also be supplied in individual containers if desired.

Components from these containers can be combined in desired amounts to provide a matrix-forming composition suitable for an intended use. Instructions for preparing the matrix-forming composition can also be included in the kit that can describe methods for preparation of one or more compositions, and methods for applying the composition and forming the matrix on a target site. The kit can also include an applicator device useful for providing the composition to a target site.

In some aspects of the invention, the matrix-forming composition is applied to a target site in situ and then treated to form a matrix of polymerized material. In performing the application, the composition is generally prepared and then applied to the site using an applicator device, such as an applicator device that includes a syringe.

Steps in forming the matrix typically involve disposing the composition in a suitable form to a target site. The composition may be disposed on a target site in any suitable manner and in a desired amount, such as by injection, painting, brushing, and spraying. In some aspects it may be desirable to provide the composition in a highly viscous form to a target site. This may allow the matrix to be formed in a precise manner, at desired locations and in a desired shape. Alternatively, castings or moldings may be used in conjunction with the matrix-forming composition to control the spread of the composition at the target site.

As indicated, the target site can be at any area of the body wherein a matrix is intended to be formed. For example, in the oral cavity, the composition can be disposed on soft tissue such as the gums, and/or the teeth.

The matrix forming compositions can also be used for cutaneous wound repair, such as in cutaneous ulcers, and used in repairing cartilage defects or damage.

The composition can be treated to activate the photoinitiator and promote polymerization and matrix formation during and/or after the composition has been disposed on the target site. For example, an amount of composition can be disposed and irradiated at the time of application, or disposed and then irradiated after application, or combinations thereof. The steps of disposing and irradiating can be performed once, or more than one time during the overall process. For example, if it is desired to build up the thickness of the matrix, the steps of disposing and irradiating can be performed multiple times during the overall process of matrix formation.

In performing the step of irradiating any suitable visible light-emitting source can be used. Commonly used visible light-emitting sources include plasma arc, conventional halogen lamps, fast halogen lamps, and LEDs. The visible light-emitting sources can be any one that is capable of generating visible light within wavelengths that promote activation of the water-soluble photoinitiator. Light sources having a wavelength from about 250 nm to about 750 nm can be used, and preferably ones that have a more specific light emission, wherein primarily visible light is emitted. For example, in many aspects light sources primarily emitting wavelengths of about 400 nm or greater are used.

Many LEDs have a relatively defined visible light emission spectrum, ranging from about 420 nm to about 530 nm, with peak emissions in the range from about 450 nm to about 490 nm. Because of this, they are ideally suited for activation of water-soluble photoinitiators such as camphorquinone, which has a peak absorption of about 470 nm. In addition, LEDs are characterized by low power consumption, efficient output, and minimal heat.

Since some commercially available LEDs have different peak emissions, an appropriate LED can be chosen based on the photoinitiator, or combinations thereof, used in the matrix-forming composition. Various types of LED shank-piece designs are available (for example, in "wand" or "gun" style); the appropriate headpiece can be chosen based on preference and/or application. Commercially available LEDs include, but are not limited to, Ultra Lume™ LED 5 (Ultradent; South Jordan, Utah); L. E. Demtron™ 1 (Kerr Corporation, Orange, Calif.), CoolBlu™ 2 (Dental Systems Intl., Ormond Beach, Fla.); LumaCure™ (LumaLite Inc., Spring Valley, Calif.); and VersaLux™ (Centrix,. Shelton, Conn.).

Halogen lights, such as Quartz Tungsten Halogen (QTH) lights are also suitable sources and generally have a light emission spectrum ranging from about 390 nm to about 530 nm. Commercially available QTH lights include, for example, Optilux 401 ™ (Kerr Corporation, Orange, Calif.).

LED/Quartz Tungsten Halogen hybrid lamps can also be used (for example, ZAP™ Dual Curing Light, CMS-Dental).

Light from the light source is applied in an amount sufficient to promote formation of the matrix of the applied composition given the components of the matrix forming composition and the light source used. Generally, the amount of energy that is applied to the disposed matrix will depend on the light intensity and duration of the light treatment. Light intensity is the amount of power distributed over a given area. Light intensity can be increased or decreased by adjusting the amount of total power, or adjusting the area of distribution of the light (for example, by the distance the light is placed from the disposed composition). Generally, LEDs provide lower intensity radiation as compared to QTH lights. For example, some commercial LEDs have light intensities that can range from about 250 mW/cm$^2$ to about 1000 mW/cm$^2$, and output powers ranging from about 150 mW to about 600 mW. Light intensity values can be obtained for any particular light source by measurement with a radiometer.

The light source can be placed a desired distance from the disposed composition. Generally, the distance that the light source is placed will depend on the spot size of the applied light and the area of the disposed composition. Typically, it is desirable to optimize the distance from the tip of the light to the disposed composition to provide the maximum intensity, thereby minimizing the cure time (i.e., time for matrix formation).

To exemplify the process of activating the photoinitiator to promote polymerization of the disposed composition, a light source having an output power of about 400 mW is held at a distance of about 10-20 mm from the disposed composition. The composition is then irradiated for a period of about 40 seconds.

The invention will be further described with reference to the following non-limiting Examples.

Example 1

Two grams of hyaluronic acid (Lifecore Biomedical, Chaska, Minn.) were dissolved in 100 ml of dry formamide. To this solution were added 1.0 g (9.9 mmol) of TEA and 4.0 g (31 mmol) of glycidyl acrylate. The reaction mixture was stirred at 37° C. for 72 hours. After exhaustive dialysis against deionized water using 12-14k MWCO dialysis tubing, the product (2.89 grams) was isolated by lyophilization.

Example 2

Acrylated HA (as prepared in example 1) in an amount of 80 mg of was added to 1 mL of PBS (pH 7.4) followed by the addition of 1.5 mg of camphorquinone-10-sulfonic acid hydrate (CQ-10-SAH; Fluka). These components were mixed for 2 hours at 37° C. on an orbital shaker. After mixing, 10 µL of t-butyl hydroperoxide (concentration 700 mg/mL) and 0.5 mg n-vinyl-sulfosuccinimide (lyophilized; prepared as described in Example 4 of U.S. Patent Application Publication No. 2005/0112086) was added and mixed on an orbital shaker at room temperature for 2-4 hours. The final concentration of reagents in the macromer composition were as follows: 80 mg/mL acrylated HA; 1.5 mg/mL CQ-10-SAH; 7 mg/mL t-butyl hydroperoxide, and 0.5 mg/ml n-vinyl-sulfosuccinimide.

The composition in an amount of 30 µL was then placed on a glass slide and illuminated for 40 seconds with a Smartlite IQ™ LED curing light (Dentsply Caulk) with a light tip to glass slide/composition distance of about 2 cm. A semi-firm gel having with elastomeric properties was formed.

Example 3

A macromer composition containing peptide was prepared and then polymerized to form a peptide-containing matrix. The macromer composition was prepared according Example 2 and had a final concentration of 8% HA, 1.5% CQ, 0.5% NVSS, and 1% TBHP. The macromer composition in an amount of 250 µL was then added to 150 mg Pepgen P-15 peptide supplied as lyophilized particulates (Dentsply Ceramed Dental, Lakewood, Colo.) and mixed with a spatula for 3 minutes at room temerprature.

The composition in an amount of 30 µL was then placed on a glass slide and illuminated for 40 seconds with a Smartlite IQ™ LED curing light with a light tip to glass slide/composition distance of about 2 cm. A semi-firm gel having with elastomeric properties was formed.

Example 4

The process as described in Example 2 was repeated, with the substitution of 0.5% n-vinyl pyrrolidone (NVP) for 0.5% NVSS. A semi-firm gel having with elastomeric properties was formed.

Example 5

Acrylated HA (as prepared in example 1) in an amount of 80 mg of was added to 1 mL of PBS (pH 7.4) followed by the addition of 1.5 mg of CQ-10-SAH. These components were mixed for 2 hours at 37° C. on an orbital shaker. After mixing, 10 µL of t-butyl hydroperoxide (concentration 700 mg/mL) was added and mixed on an orbital shaker at room temperature for 2-4 hours. The concentration of reagents in the macromer composition were as follows: 80 mg/mL acrylated HA; 1.5 mg/mL CQ-10-SAH; 7 mg/mL t-butyl hydroperoxide.

The composition in an amount of 30 µL was then placed on a glass slide and illuminated for 40 seconds with a Smartlite IQ™ LED curing light with a light tip to glass slide/composition distance of about 2 cm. A semi-firm gel having with elastomeric properties was formed.

Example 6

Five grams of Bovine Type 1 Collagen (Kinsey-Nash Corp., Exton, Pa.) was dissolved in 1700 ml of 0.012 N hydrochloric acid and stirred for 4 hours at 4° C. To this solution was added 3 grams of sodium-carbonate (Sigma) and 11.76 g sodium-bicarbonate (Sigma) and mixed for 60 minutes at 4° C. To this solution was added 350 mg acrylic acid N-hydroxysuccinimide (Sigma). The reaction mixture was stirred at 4° C. for 24 hours. After exhaustive dialysis against deionized water using 6-8k MWCO dialysis tubing, the product (4.93 grams) was isolated by lyophilization.

Example 7

Acrylated collagen macromer (as prepared in example 6) in an amount of 45 mg was added to 1 mL of PBS (pH 7.4) followed by the addition of 1.5 mg of CQ-10-SAH (Fluka). These components were mixed for 2 hours at 37° C. on an orbital shaker. After mixing, 10 µL of t-butyl hydroperoxide (concentration 700 mg/mL) was added and mixed on an orbital shaker at 37° C. for 30 minutes. The concentration of reagents in the macromer composition were as follows: 45 mg/mL Collagen Macromer; 1.5 mg/mL CQ-10-SAH; 7 mg/mL t-butyl hydroperoxide.

The composition in an amount of 30 μL was then placed on a glass slide and illuminated for 40 seconds with a Smartlite IQ™ LED curing light with a light tip to glass slide/composition distance of about 2 cm. A semi-firm gel having with elastomeric properties was formed.

Example 8

Acrylated HA (as prepared in example 1) in an amount of 40 mg, and 30 mg of acrylated collagen (as prepared in example 7) were added to 1 mL of PBS (pH 7.4) followed by the addition of 1.5 mg of CQ-10-SAH (Fluka). These components were mixed for 2 hours at 37° C. on an orbital shaker. After mixing, 10 μL of t-butyl hydroperoxide (concentration 700 mg/mL) was added and mixed on an orbital shaker at 37° C. for 60 minutes. The concentration of reagents in the macromer composition were as follows: 40 mg/mL acrylated HA; 30 mg/mL Collagen Macromer; 1.5 mg/mL CQ-10-SAH; 7 mg/mL t-butyl hydroperoxide.

The composition in an amount of 30 μL was then placed on a glass slide and illuminated for 40 seconds with a Smartlite IQ™ LED curing light with a light tip to glass slide/composition distance of about 2 cm. A semi-firm gel having with elastomeric properties was formed.

We claim:

1. A method for forming a matrix in situ in a periodontal procedure, comprising the steps of (a) applying a matrix-forming periodontal composition to a tissue in the oral cavity, the composition comprising (i) a macromer comprising a polysaccharide and (ii) a water-soluble diketone photoinitiator having an activation wavelength of 400 nm or greater; and (b) treating the composition to activate the diketone photoinitiator and promote formation of a matrix.

2. The method of claim 1 wherein the diketone photoinitiator has an activation wavelength in the range of 440 nm to 500 mm.

3. The method of claim 2 wherein the diketone photoinitiator is water-soluble camphorquinone.

4. The method of claim 1 wherein the macromer comprises hyaluronic acid.

5. The method of claim 1 wherein the macromer is present at a concentration in the range of 50 mg/mL to 100 mg/mL.

6. The method of claim 1 wherein the composition has a viscosity of about 500 cP or greater.

7. The method of claim 1 wherein the composition comprises a peroxide or hydroperoxide co-initiator.

8. The method of claim 1 wherein the composition comprises an alkyl hydroperoxide co-initiator.

9. The method of claim 7 wherein the co-initiator is present at a concentration of 7 mg/mL or greater.

10. The method of claim 1 wherein step (b) comprises activating the diketone photoinitiator with a visible-light emitting source selected from the group consisting of plasma arc sources, conventional halogen lamps, fast halogen lamps, and LEDs.

11. The method of claim 1 wherein the composition comprises a bioactive agent.

12. The method of claim 11 wherein the bioactive agent comprises a bioactive peptide.

13. The method of claim 12, wherein the bioactive peptide comprises a bioactive collagen peptide.

14. The method of claim 1, wherein the composition comprises filler particles.

15. The method of claim 1, wherein the composition does not include a tertiary amine co-initiator.

16. The method of claim 1, wherein the macromer has a molecular weight of $1\times10^5$ Da or greater.

17. A polymerizable composition for in situ use comprising a macromer, comprising a polysaccharide and a water-soluble diketone polymerization photoinitiator having an activation wavelength of greater than 400 nm, wherein the composition has a viscosity of 500 cP or greater.

18. A method for providing a matrix in situ comprising the steps of (a) providing a matrix-forming composition to a surface, the composition including a (i) macromer comprising a polysaccharide and (ii) a water soluble visible light activated diketone photoinitiator, and (b) activating the photoinitiator to promote formation of the matrix with a LED source having a peak emission wavelength of greater than 400 nm.

19. The method of claim 1 wherein the diketone photoinitiator comprises a charged group.

20. The method of claim 3 wherein the diketone photoinitiator is camphorquinone-10-sulfonic acid.

21. The polymerizable composition of claim 17 wherein the diketone photoinitiator is camphorquinone-10-sulfonic acid.

* * * * *